United States Patent
Chiu et al.

(10) Patent No.: US 7,524,409 B2
(45) Date of Patent: Apr. 28, 2009

(54) METHOD AND SYSTEM FOR ELECTROKINETIC, PREPARATIVE SAMPLE SEPARATION IN HIGH-SURFACE-AREA SEPARATION CHANNELS WITH NON-CONVEX CROSS SECTIONS

(75) Inventors: Daniel T. Chiu, Seattle, WA (US); Jason S. Kuo, Seattle, WA (US); David S. W. Lim, Seattle, WA (US)

(73) Assignee: University of Washington, Seattle, WA (US)

( * ) Notice: Subject to any disclaimer, the term of this patent is extended or adjusted under 35 U.S.C. 154(b) by 943 days.

(21) Appl. No.: 10/846,147

(22) Filed: May 14, 2004

(65) Prior Publication Data

US 2005/0003411 A1    Jan. 6, 2005

Related U.S. Application Data

(60) Provisional application No. 60/471,270, filed on May 15, 2003.

(51) Int. Cl.
   *B81B 1/00* (2006.01)
(52) U.S. Cl. .............. 204/601; 204/600; 422/312; 422/944; 138/121
(58) Field of Classification Search .......... 204/600, 204/601; 422/312, 944; 138/121
   See application file for complete search history.

(56) References Cited

U.S. PATENT DOCUMENTS

| | | | |
|---|---|---|---|
| 5,324,413 A * | 6/1994 | Gordon | 204/603 |
| 5,522,974 A | 6/1996 | Fishel et al. | 264/104 |
| 5,534,123 A | 7/1996 | Bashkin et al. | 204/455 |
| 5,858,188 A | 1/1999 | Soane et al. | 204/454 |
| 6,207,049 B1 * | 3/2001 | Abdel-Rahman | 210/198.2 |
| 6,322,682 B1 | 11/2001 | Arvidsson et al. | 204/454 |
| 6,322,736 B1 | 11/2001 | Bao et al. | 264/105 |

OTHER PUBLICATIONS

Jo, B.-Y., et al. "Three-dimensional Micro-channel Fabrication in Polydimethylsiloxane (PDMS) Elastomer", Journal of Microelectromechanical Systems, vol. 9, No. 1, Mar. 2000, pp. 7681.*

Byung-Ho, Jo et al., *Three-dimensional micro-channel fabrication in polydimethylsilozane (PDMS) elastomer*, Journal of MIcroelectromechanical Systems, 2000, vol. 9, Issue 1, Abstract.

* cited by examiner

*Primary Examiner*—Alex Noguerola
*Assistant Examiner*—J. Christopher Ball
(74) *Attorney, Agent, or Firm*—Olympic Patent Works PLLC

(57) ABSTRACT

Embodiments of the present invention employ complexly shaped, high-surface-area channels for separation and purification of molecules, including important biopolymers such as proteins, glycoproteins, polysaccharides, and other molecular components of living cells. The relatively large internal surface areas of the complexly shaped channels employed in embodiments of the present invention provide, in comparison to traditional, simply shaped separation channels, increased heat dissipation during electrokinetic separation, and a decreased tendency for bulk-solution flow. Heat dissipation prevents high temperatures that can denature proteins and that can induce thermal currents within the separation channel. Bulk-solution flow within a separation channel can overwhelm the generally linear, electrical-potential-induced migration of molecules that leads to efficient and well-resolved molecular separations. The complexly shaped channels employed in various embodiments of the present invention can be readily manufactured at microscale dimensions for use in microscale devices, at millimeter-scale dimensions for inclusion in microfluidics devices, and may also be used in larger scale, traditional separation and purification systems.

15 Claims, 13 Drawing Sheets

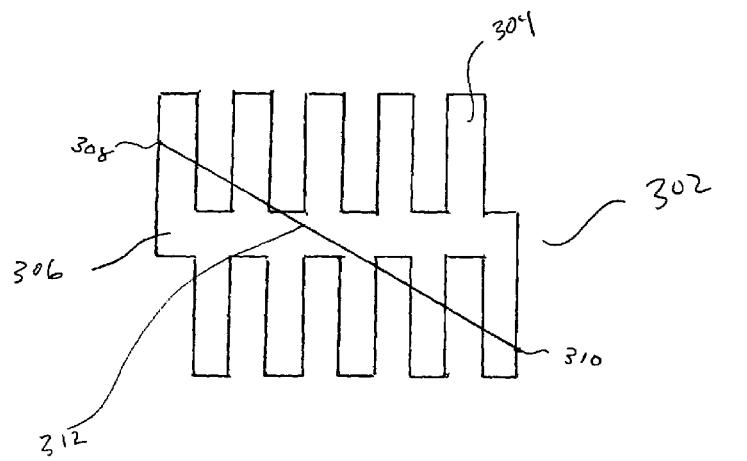
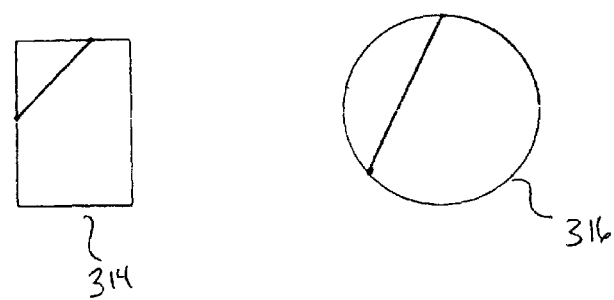
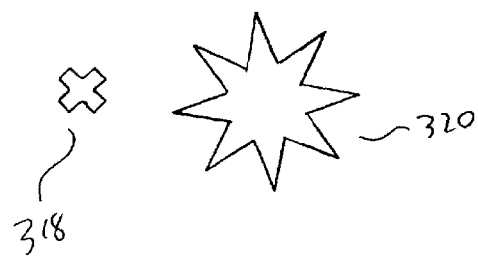
Figure 3

US 7,524,409 B2

METHOD AND SYSTEM FOR ELECTROKINETIC, PREPARATIVE SAMPLE SEPARATION IN HIGH-SURFACE-AREA SEPARATION CHANNELS WITH NON-CONVEX CROSS SECTIONS

CROSS-REFERENCE TO RELATED APPLICATION

This application claims the benefit of provisional Application No. 60/471,270, filed May 15, 2003.

TECHNICAL FIELD

The present invention is directed to methods and systems for isolating relatively pure solutions of the different molecular species initially contained as complex mixtures in sample solutions and, in particular, to methods and systems for efficiently and efficaciously preparing relatively large quantities of relatively pure solutions of single molecular species from complex solutions.

BACKGROUND OF THE INVENTION

In the past five years, enormous progress has been made in elucidating the identities of the molecular components of many living organisms, including humans. Completion of the initial phases of the human genome project have provided a detailed DNA sequence for a large portion of human chromosomal DNA. However, the determination of the DNA sequence of human chromosomes is only a preliminary initial step in the identification of the molecular components of human cells, which is, in turn, only an initial step in understanding how these molecular components interact with one another to form a functioning cell. Different portions of chromosomal DNA, or chromosome subsequences, play different roles in information storage and control of cellular processes, and many portions may play different roles at different times and under different intercellular and intracellular conditions. Perhaps the best-known role for chromosomal subsequences is that of genes. A gene is a stretch of DNA that more or less directly encodes the amino-acid sequence of a corresponding protein. Proteins are biopolymers responsible for myriad structural, catalytic, and control functions in living cells.

Initial analysis of the human DNA sequence led to the conclusion that a total of only about 30,000 proteins are encoded in human DNA. However, many researchers currently believe that a far greater number of proteins may actually be encoded. First, it is possible that only a fraction of the total number of genes has been identified. Second, and more importantly, many different cellular processes can dynamically edit and alter DNA encodings to produce a much larger number of amino-acid-sequence specifications, or mRNA templates, than can be statically identified in chromosomal DNA. Moreover, post-translational processing of nascent proteins can lead to even greater numbers of different types of proteins, as well as many different hybrid and derivative proteins that include significant non-amino-acid components, such as lipid and polysaccharide components, as well as non-standard amino acids.

Determining the identities of, and characterizing, the different protein species in living cells, commonly referred to as the field of proteomics, represents a next phase in understanding the components and processes within living cells. Although it was, at one time, thought that the identities and characteristics of the protein components of living cells might be computationally determined from a complete sequence of the chromosomal DNA, it is now apparent that biochemical isolation and characterization of physical protein molecules remains a necessary approach to identifying and characterizing the protein components of living cells.

A number of different physical techniques are currently employed to identify and characterize proteins. Proteins are identified by separating and identifying individual protein species from complex mixtures of different types of proteins, other types of biopolymers, and small molecules. A particular protein is characterized by its amino-acid sequence, by the one or more native three-dimensional configurations that the protein adopts in its natural, cellular environment, and by its location and function in a cell or in extracellular solutions. Determination of the amino-acid sequence and the three-dimensional configuration of a protein both depend on preparing a relatively pure solution of the protein at relatively high concentrations, in the 5-25 mg./ml. range. For example, pure proteins may be crystallized, and the protein structure determined by x-ray diffraction techniques. Protein crystallization generally involves slow supersaturation of highly purified and concentrated protein solutions. Additional structure determination techniques include nuclear magnetic resonance and spectroscopic techniques, both of which also require relatively pure, concentrated protein solutions. Unfortunately, any particular human cell lysate may contain 20,000 or more proteins with concentrations spanning five or more orders of magnitude. Therefore, for now and for the foreseeable future, the identification and characterization of the protein components of living cells both depend on the development of efficient and precise methods for preparing relatively large amounts of pure proteins from highly complex sample solutions.

Many different types of protein separation and purification techniques are currently used. These techniques include high performance liquid chromatography ("HPLC"), exclusion and affinity chromatography, capillary electrophoresis, and other techniques. Currently used techniques all have various advantages and disadvantages. For example, HPLC provides high throughput and time-efficient separations, but the resolution of HPLC separations may suffer from dispersion due to position-dependent fluid-flow-velocity differentials within HPLC columns. Moreover, the matrix within an HPLC column, by showing differential affinity or exclusion towards different types of proteins, may significantly impact the resolution and overall separability of proteins within a sample solution. An additional disadvantage of the HPLC technique is that proteins may partially or fully unfold from their native three-dimensional configurations as they pass through the HPLC column and interact with the column matrix, and protein unfolding is often practically irreversible. Traditional capillary electrophoresis provides fast and sensitive protein separation, but is restricted to relatively small sample sizes, in the nanoliter range.

Researchers, drug developers, and other professionals involved in identifying and characterizing proteins and other molecular components of living cells have therefore recognized the need for improved methods for separating and purifying significant quantities of proteins and other biopolymers. In particular, methods that can be implemented in microfluidic devices as well as in traditional, larger-scale separation and purification instruments, are highly desirable.

SUMMARY OF THE INVENTION

Embodiments of the present invention employ complexly shaped, high-surface-area channels for separation and purification of molecules, including important biopolymers such as proteins, glycoproteins, polysaccharides, and other molecular components of living cells. The relatively large internal surface areas of the complexly shaped channels employed in embodiments of the present invention provide, in comparison to traditional, simply shaped separation channels, increased heat dissipation during electrokinetic separation, and a decreased tendency for bulk-solution flow. Heat dissipation prevents high temperatures that can denature proteins and that can induce thermal currents within the separation channel. Bulk-solution flow within a separation channel can overwhelm the generally linear, electrical-potential-induced migration of molecules that leads to efficient and well-resolved molecular separations. The complexly shaped channels employed in various embodiments of the present invention can be readily manufactured at microscale dimensions for use in microscale devices, at millimeter-scale dimensions for inclusion in microfluidics devices, and may also be used in larger scale, traditional separation and purification systems.

BRIEF DESCRIPTION OF THE DRAWINGS

FIGS. 1A-E illustrate ideal, channel-based molecular separation and purification and problems associated with separation and purification.

FIG. 3 illustrates the difference between non-convex cross-sections and convex cross-sections, and provides examples of additional non-convex cross-sections.

DETAILED DESCRIPTION OF THE INVENTION

Embodiments of the present invention employ complexly shaped separation channels, including microchannels within microfabricated devices as well as macroscale channels in traditional sample separation and purification equipment, in order to more efficiently and effectively carry out molecular separations and purifications. The complexly shaped channels of the present invention are described, below, following a general discussion of problems associated with the currently employed rectangular and cylindrical separation channels.

Figure 1A:
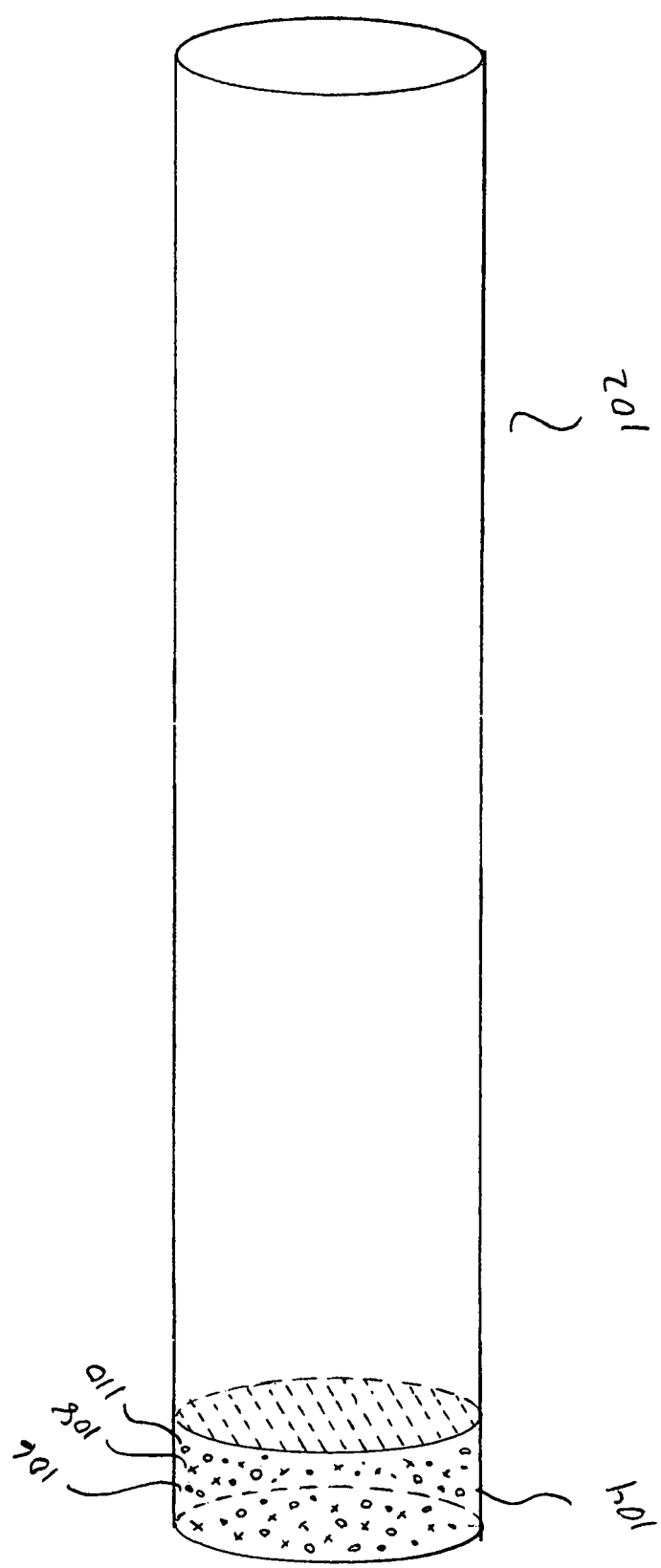

FIGS. 1A-E illustrate ideal, channel-based molecular separation and purification and problems associated with separation and purification. FIG. 1A shows a hypothetical, ideal separation channel having a convex cross-section. The separation channel 102 is a thin-walled cylindrical tube, generally made of glass or fused quartz, containing a buffered aqueous solution and, depending on the separation technique, additionally containing an immobile stationary phase such as a hydrated polymer or gel. A sample solution 104 has been introduced at the left end of the separation channel so that the sample solution inhabits a small, cylindrical region of the separation channel. In practice, sample solutions are often introduced to produce an extremely thin, disc-like, highly concentrated sample-containing volume, in order to facilitate formation of distinct, well-separated bands, as discussed below. In the hypothetical separation illustrated in FIGS. 1A-D, the sample solution includes three different molecular species, designated by (1) filled disks, such as filled disk 106; (2) crosses, such as cross 108; and (3) unfilled disks, such as unfilled disk 110. The intent of a separation procedure is to resolve the mixture 104 into three different regions, each containing only one of the three different molecular species. Of course, in real-world separations and purifications, a sample solution may be extremely complex, containing hundreds or thousands of different molecular species.

Figure 1B:
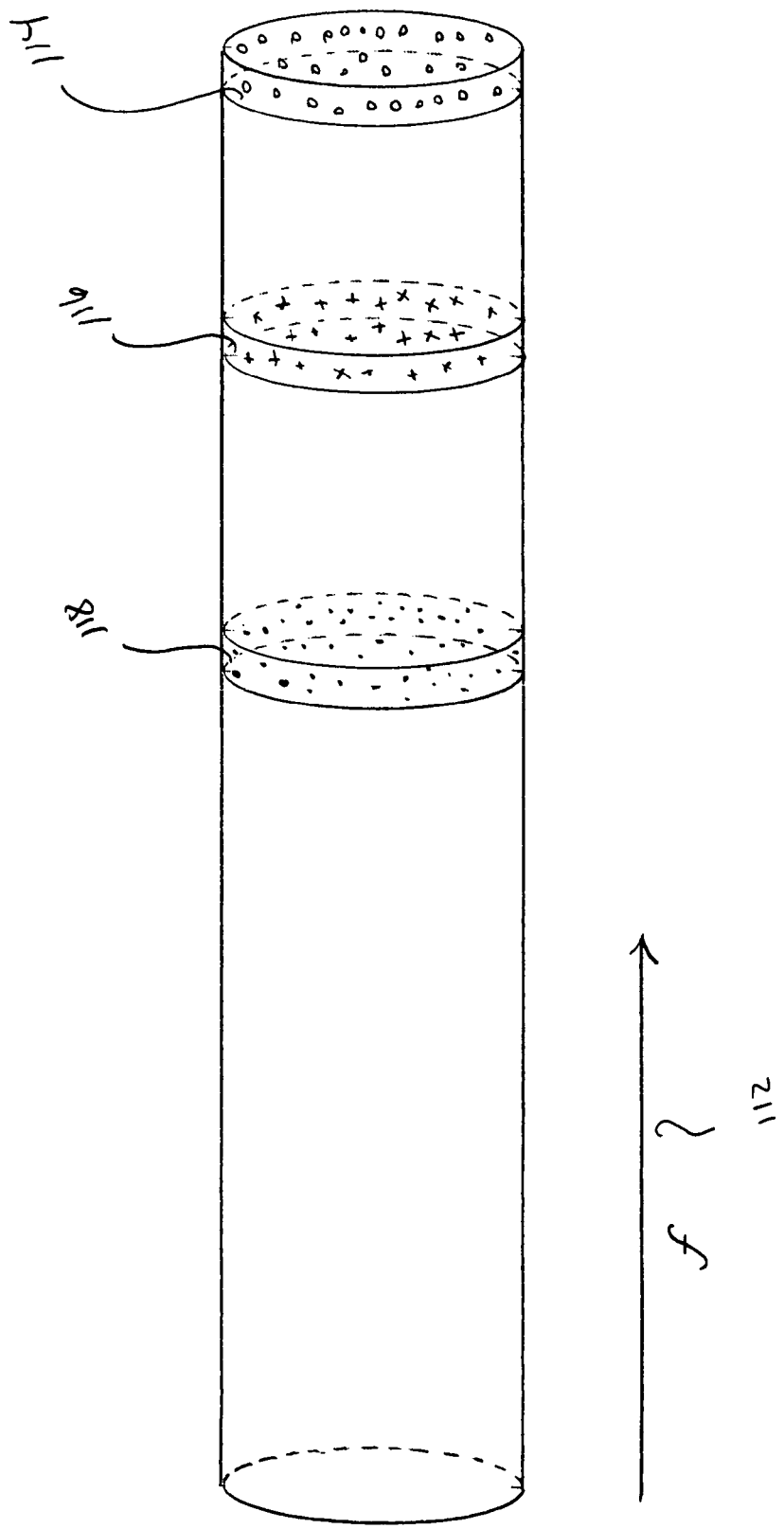

In an ideal separation procedure, as shown in FIG. 1B, a force 112 is applied to the contents of the separation channel that results in migration of the molecular components of the sample solution in one direction along the length of the separation channel, each different molecular species exhibiting a different, characteristic mobility within the separation-channel matrix. Because of the different, characteristic mobilities of the different molecular species, as the molecular species migrate rightward, in the example shown in FIG. 1B, the different molecular species tend to separate from one another in distinct, small cylindrical regions, or bands. For example, in FIG. 1B, the molecular species represented by unfilled disks exhibits the greatest mobility, and ends up, after a period of time, concentrated in the plug-like cylindrical region 114 at the right-hand end of the separation channel. The molecular species represented by crosses has a smaller mobility, and therefore ends up, after the period of time, within a cylindrical plug 116 displaced leftward from the cylindrical plug 114 containing the highest mobility molecular species. The molecular species represented by filled disks, having the lowest mobility within the separation-channel matrix, ends up in a cylindrical-plug region 118 even further displaced from the right-hand end of the separation channel.

A separation channel may be used for identification of the components of a complex solution, for purification of the different molecular species within a complex solution, or for both identification and purification. For example, the plug-like cylinders 114, 116, and 118 inhabited by the different molecular species following a force-induced migration along the length of the separation channel may be detected by spectrometry or other analytic techniques within a separation channel and compared to known or calculated locations for known molecular species in order to identify the species originally present in the sample solution. When the mobilities of the molecular species depend on molecular size and shape, the approximate size and shapes of unknown species within the sample solution can be interpolated from the locations of the corresponding cylindrical plugs, or bands, within the separation channel, with respect to actual or calculated locations for known, molecular species. Samples comprising digests of a pure biopolymer may be separated in a separation channel in order to determine the subunit sequence of the biopolymer. Because the different molecular species end up in different bands within the separation channel, the different bands may be eluted from the separation channel by continued application of the force 112 in order to obtain relatively pure solutions of the different molecular species.

Various different types of forces are used in different separation and purification techniques in order to induce migration of a molecular species along a separation channel. In the HPLC technique, the force is an externally applied hydrodynamic pressure which forces the mobile, fluid phase within the separation channel through a relatively immobile, stationary phase. Different levels of affinity of the molecular species for the stationary phase, as well as the ability of different molecular species to enter into, and migrate through, the stationary phase, may result in different mobilities of molecular species within the separation channel.

In the capillary electrophoresis technique, the separation channel traditionally contains a fluid matrix, generally a buffered, electrolyte solution. An applied electrical potential provides the force that induces migration of molecular species within the sample solution along the length of the separation channel. The applied electric potential causes negatively charged species to migrate towards the anode and positively charged species to migrate towards the cathode under a force proportional to the amount of charge carried by the molecule. The electromotive force is opposed by a frictional force arising from molecular interactions between sample molecules and the separation-channel matrix, as well as from the need for the sample molecule to displace solvent as the sample molecule migrates. An electrophoretic mobility for a particular molecular species reflects the balance between the electromotive force and the opposing frictional force. The applied electrical field also induces an electroosmotic force within the separation channel that results in bulk flow of the fluid within the separation channel towards either the anode or cathode. When the surface of the separation channel is relatively negatively charged, as is the case for glass, a positively charged fluid layer develops near the surface of the separation channel. The applied electrical field causes the positively charged fluid layer to move towards the cathode, and intermolecular forces within the fluid result in bulk fluid flow in the same direction. Similarly, when the surface of the separation channel is positively charged, a negatively charged fluid layer forms near the surface, and is induced to flow towards the anode of the applied electrical potential, dragging along the bulk matrix solution. Note that the electroosmotic and electrophoretic forces may be commonly oriented, or may oppose one another, depending on the nature of the surface of the separation channel and of the molecular species. Each molecular species therefore has an overall mobility within the separation channel under an applied electrical potential equal to the sum of the molecular species' electrophoretic and electroosmotic mobilities.

When the molecular species in a sample migrate within a separation channel in well-defined, plug-like cylindrical regions, as shown in FIG. 1B, very high-resolution separations can be achieved, resulting in efficient identification of different molecular species and efficient isolation of relatively pure samples of each molecular species within the sample solution. However, for a variety of reasons, the ideal, plug-like migration shown in FIG. 1B may be obtained only under very special conditions. Many different physical phenomena may conspire to alter or disrupt fluid flow within a separation channel, leading to dispersion of a molecular species within large and irregularly shaped regions of the separation channel. For example, in both pressure-driven and electroosmotically driven separations, the fluid velocity within a separation channel may not be uniform, but may instead depend on the distance of a volume element from the center of the separation channel.

Figure 1C:
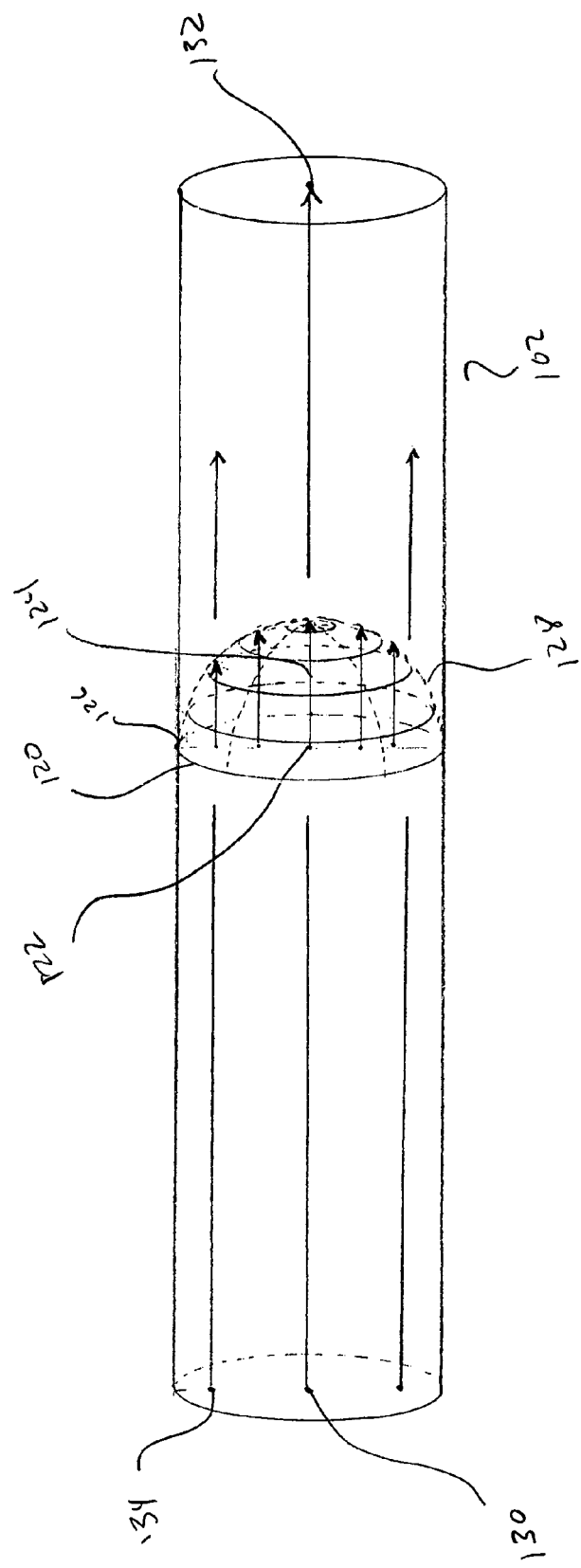

In FIG. 1C, a parabolic fluid-velocity profile is illustrated. Examining the velocities of fluid elements within a disk-like cross-section 120 of the separation channel 102, it can be determined that the velocity of the fluid element at the center of the cross-section 122 is greatest, represented by the velocity vector 124 of largest magnitude emanating from the central volume element, while the velocity of a fluid element adjacent to the surface of the separation channel 126 is nearly zero. The velocity vectors perpendicular to the cross-section may form a parabolic surface 128 perpendicular to, and downstream from, the cross-section disc as shown in FIG. 1C. The shape and curvature of the velocity profile depends on the amount of force applied, as well as on the chemical nature of the surface of the separation channel and of the fluid within the separation channel.

Figure 1D:
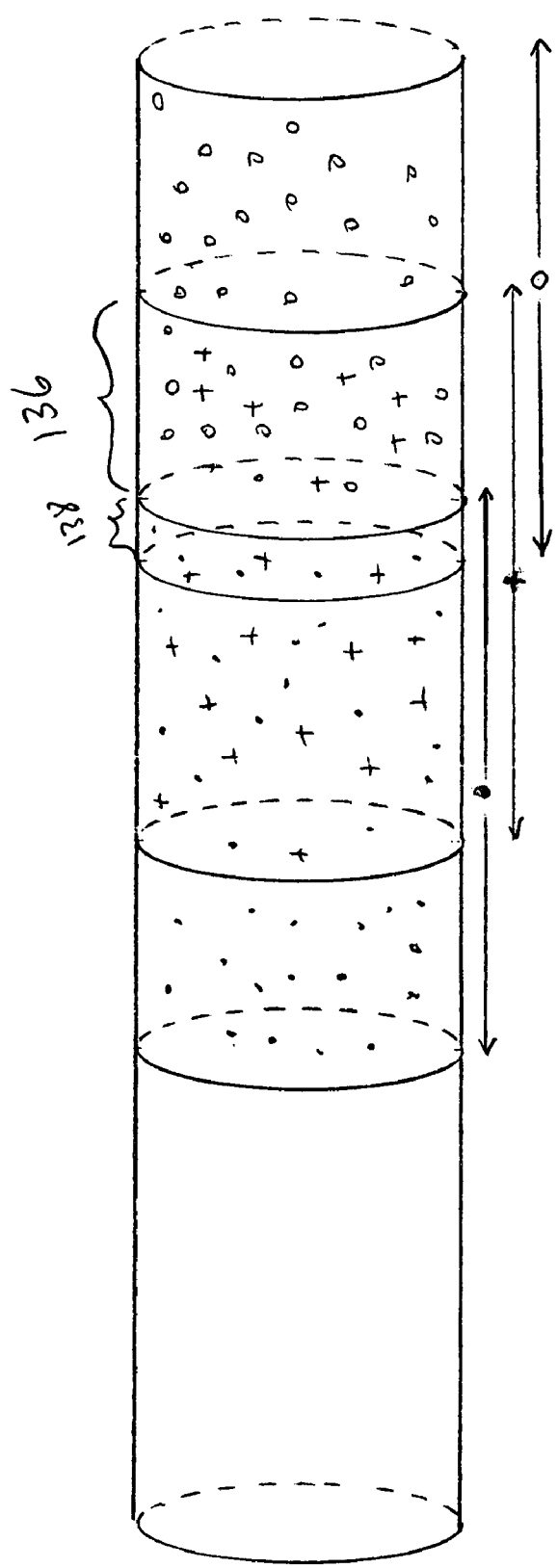
Figure 16:
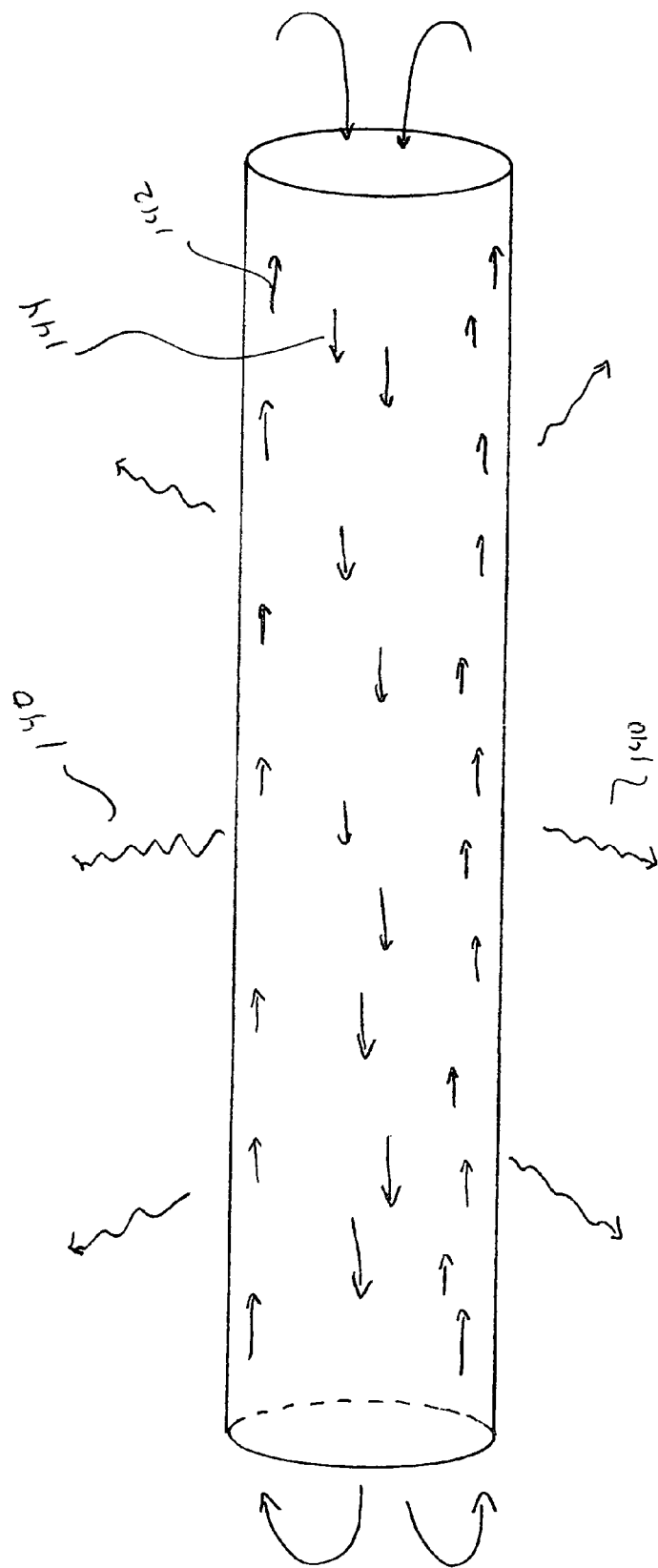

As a result of the parabolic fluid velocity profile within the separation channel of FIG. 1C, a molecule beginning at the central position of a leftmost cross-section 130 and migrating within the central portion of the separation channel migrates significantly further 132 than the same molecule beginning at a position 134 closer to the wall of the separation channel. Molecular species may diffuse laterally as well as migrate axially along the separation channel, resulting in a more diffuse, less predictable volume inhabited by the molecular species following migration through the separation channel, but non-uniform fluid velocities within the separation channel generally result in significantly more dispersed, and lower resolution bands, as shown in FIG. 1D. In FIG. 1D, each of the three molecular species, due to the dispersive effects of non-uniform fluid velocity, ends up occupying a much longer cylindrical region of the separation channel following induced migration than in the ideal separation shown in FIG. 1B. Although each molecular species migrates with its characteristic mobility within the separation channel, the dispersive effects of non-uniform fluid velocity result in significant overlapping of the final volumes occupied by the molecular species. For example, in cylindrical volume 136 in FIG. 1D, both the molecular species indicated by unfilled circles and by crosses can be found, while in volume 138, all three molecular species can be found. Overlapping of bands prevents elution of pure sample solutions from the separation channel. The lengthening of the bands also results in elution of less concentrated sample solutions.

FIG. 1E illustrates additional phenomena that may conspire to frustrate high resolution separation by capillary electrophoresis. First, application of electrical potential to the separation channel in order to induce electrophoretic and electroosmotic migration results in production of heat 140 within the separation-channel fluid. The amount of heat produced, referred to as the Joule heating, is proportional to the fourth power of the radius of the separation channel, in the case of a cylindrical separation channel such as that shown in FIGS. 1A-E. The heat can denature proteins and other biopolymers, and can generate thermal currents resulting in bulk-fluid currents. Second, a lack of hydrodynamic resistance within the capillary can result in siphoning, essentially induction of bulk-fluid currents within the separation channel 142 and 144. Such bulk-fluid currents within the separation channel result in mixing of the fluid volume and of the sample molecules, overwhelming the electrophoretic-migration-based separation of molecular species.

While HPLC techniques can be used for preparative purification of relatively large samples of proteins and other biopolymers, traditional capillary electrophoresis has been limited to small-volume, small-quantity analytic separations. In order to achieve preparative capillary electrophoresis separations, the volume of the separation channel needs to be increased, generally by increasing the radius or cross-sectional dimension of the separation channel. However, as discussed above, the heat generated by application of an electrical potential to the separation channel is proportional to the fourth power of the capillary radius. Thus, increasing the capillary radius vastly increases the heat generated within the separation channel, raising the temperature of the matrix. Similarly, the hydrodynamic resistance to fluid flow within a capillary decreases proportionally to the fourth power of the radius of the capillary. Thus, increasing the radius of a capillary leads to a spectacular decrease in fluid-flow resistance, leading to siphoning. For these reasons, capillary electrophoresis has been limited to relatively small bore capillaries, on the order of 50 micrometers, and therefore limited to extremely small-volume, nanoliter-range sample solutions. In addition, heating produced by the applied electrical potential may lead to denaturing of proteins, in turn leading to capillary blockage, unpredictable and dynamically changing molecular species mobilities, and eventual elution of uselessly impure solutions of denatured protein. On the other hand, HPLC techniques, while providing for preparative-volume separations and purifications, suffers disadvantages inherent from parabolic fluid velocity profiles and partial or complete protein denaturing.

Because of the potentially high separation efficiency and short separation times inherent in capillary electrophoresis, continuing attempts have been made to scale up capillary electrophoresis to semi-preparative and preparative separation-channel volumes. Techniques for scaling up capillary electrophoresis are directed at ameliorating the production of heat and disruptive solution currents resulting from siphoning and heat dissipation. These techniques have included external cooling, use of organic buffers with low conductance background electrolytes, and use of stationary phases within large-bore capillaries, including stationary phases comprising silicon frits. Although a certain amount of success has been obtained at semi-preparative scales, general applicability for these techniques has been limited both by increased potential for protein denaturation and by complexity in operation and implementation.

Methods of systems of the present invention employ relatively complexly shaped separation channels with non-convex cross-sections in order to greatly increase the surface-to-volume ratio of the separation channel with respect to traditional, simply shaped separation channels with convex cross-sections, such as cylindrical tubes and rectangular channels. Complexly shaped separation channels with non-convex cross-sections allow the volume of the separation channel to be increased without decreasing the surface-to-volume ratio. The greater surface-to-volume ratios provided by complexly shaped separation channels provide markedly increased heat dissipation, similar to the heat dissipation achieved by fins on radiators, and greatly increases the hydrodynamic resistance to bulk fluid flow within the separation channel. Thus, complexly shaped separation channels with non-convex cross-sections ameliorate the increased heat production and decreased resistance to fluid flow that result from increasing the volumes of simply shaped, traditional separation channels.

In certain embodiments of the present invention, the complexly shaped separation channels are produced at microscale dimensions for incorporation within microfluidic devices. Microfluidic-based separations may be critical in high-throughput protein separations needed to facilitate proteomics research, as discussed above. In one application, microfluidics-based automated crystallization systems are planned for surveying the state spaces of crystallization conditions for various biopolymers in order to vastly increase the number of proteins that can be characterized by X-ray diffraction techniques.

Figure 2A:
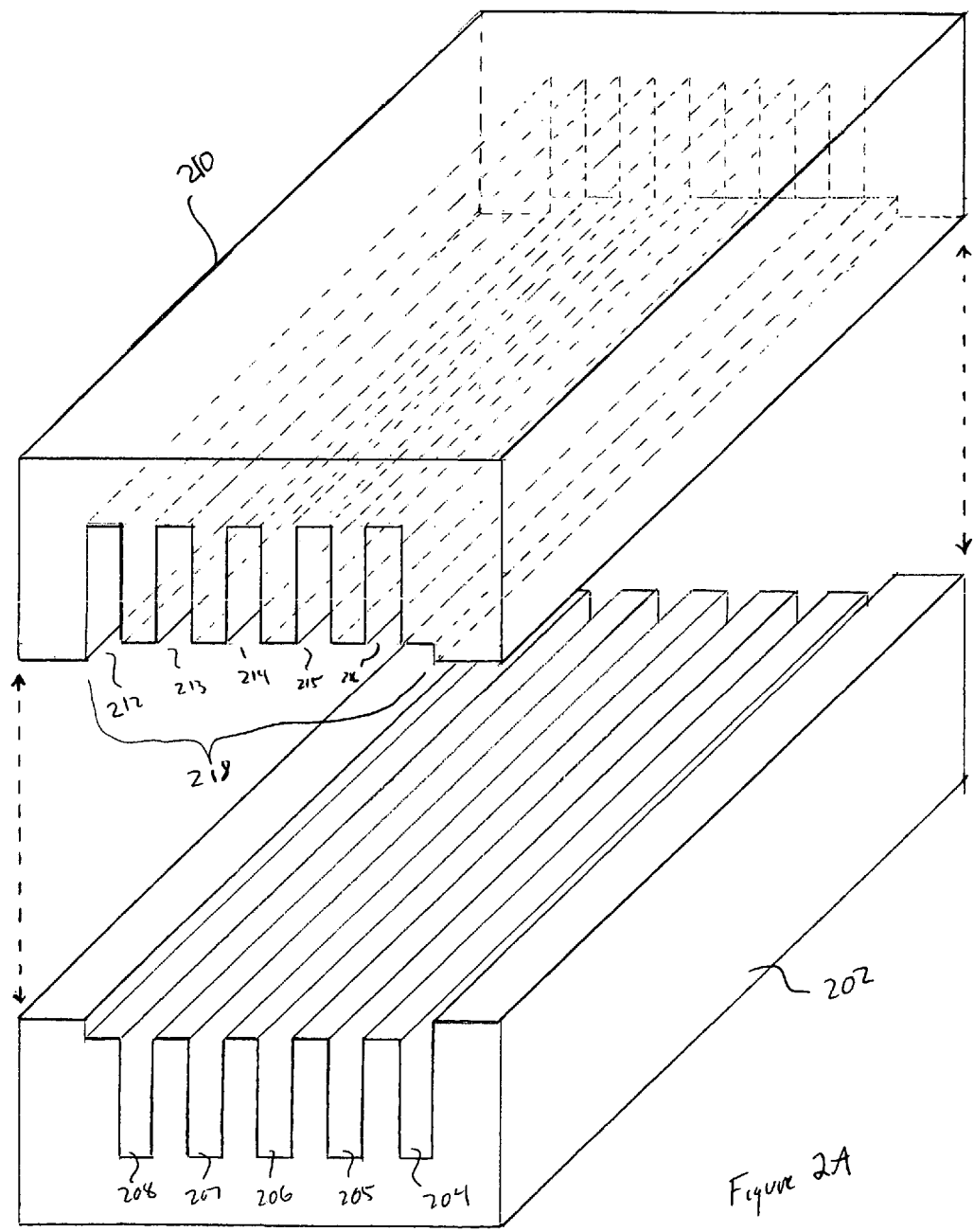
FIGS. 2A-B illustrate a portion of a microscale, complexly shaped separation channel that represents one embodiment of the present invention.
Figure 2B:
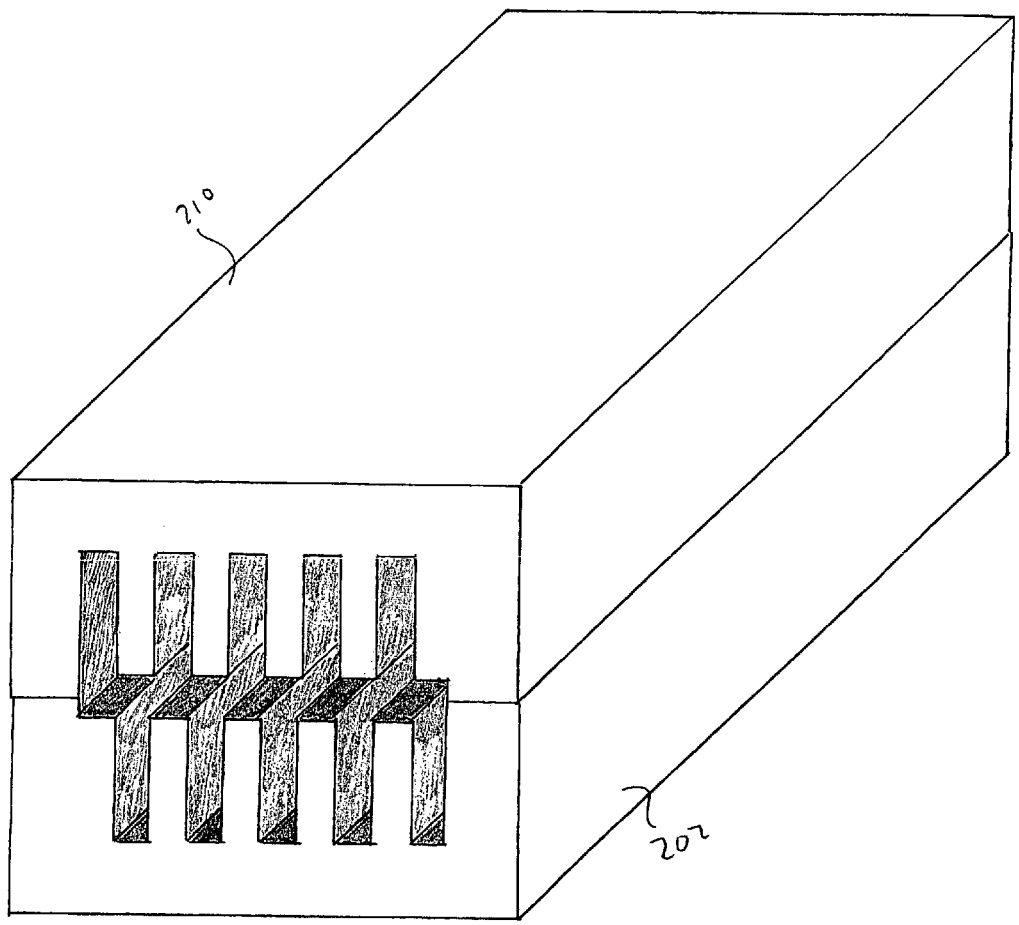

FIGS. 2A-B illustrate a portion of a microscale, complexly shaped separation channel that represents one embodiment of the present invention. In FIG. 2A, a polydimethylsiloxane ("PDMS") lower slab 202 containing five linear invaginations 204-208, or slots, is oriented with respect to an upper PDMS slab 210 containing five similar linear invaginations 212-216, or slots, laterally offset from those of the lower slab 204-208. In both the lower and upper slabs 202 and 210, the slots occur within a wider, shallow, rectangular slot, such as the shallow, rectangular slot 218 in the upper slab 210. As shown in FIG. 2B, the lower and upper PDMS slabs 202 and 210 can be joined together and sealed to produce a complexly shaped separation channel within the PDMS block running the length of the rectangular PDMS block. The complexly shaped separation channel shown in FIG. 2B features 10 PDMS fins. Similar complexly shaped separation channels can be produced with different numbers of fins.

FIG. 3 illustrates the difference between non-convex cross-sections and convex cross-sections, and provides examples of additional non-convex cross-sections. The cross-section 302 for the complexly shaped separation channel shown in FIG. 2B is shown at the top of FIG. 3. The complexly shaped separation channel can be seen to be composed of ten narrow, vertical channels, such as vertical channel 304, all joined together by a central, horizontal channel 306. This cross-section is non-convex because there exists at least two points 308 and 310 on the outer boundary of the cross-section such that, when a straight line is drawn between the two points 308 and 310, the straight line 312 includes sections internal to the cross-section as well as sections external to the cross-section. In other words, in the multi-finned cross section 302 for the example separation channel shown in FIG. 2B, the straight line between points 308 and 310 passes through both interior channel regions and the PDMS fins. By contrast, currently available separation channels have simple, convex cross-sections, such as rectangles 314 and circles 316. In convex cross-sections, a straight line between any two points on the boundary of the cross-section is fully contained within the interior of the cross-section.

The number of possible complex, non-convex cross-sections is practically unlimited. Two additional non-convex cross-sections 318 and 320 are shown in FIG. 3. In the simplest convex cross-section, the circle 316, the surface-to-volume ratio of the separation channel is inversely related to the radius of the cross-section. However, using non-convex cross-sections, a separation channel of arbitrary volume can be designed to have any chosen surface-to-volume ratio greater than the minimum surface-to-volume ratio of a cylindrical separation channel. Of course, in the case of a rectangular cross-section, an arbitrary surface-to-volume ratio can be achieved by increasing the aspect ratio of the rectangular cross-section. However, when the aspect ratio of the cross-section increases past a certain point, the effects of lateral diffusion, the difficulties of applying uniform force over an extended, cross-sectional dimension, and the difficulties and expense in manufacturing such high-aspect-ratio separation channels conspire to constraining cross-sectional aspect ratios within severe upper limits. Non-convex cross-sections provide for much great flexibility in increasing separation channel volumes without decreasing the surface-to-volume ratios.

Figure 4:
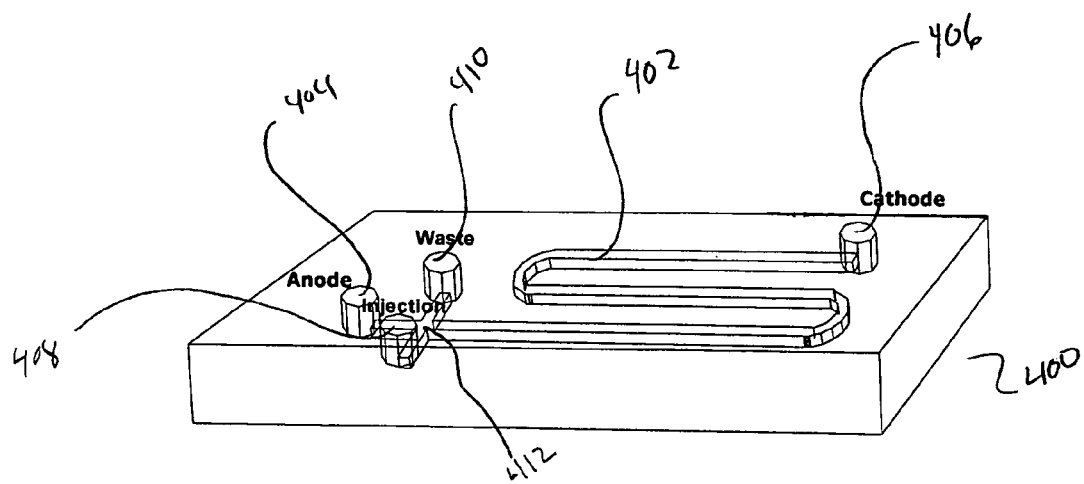
FIG. 4 illustrates a representative subunit of a microfluidic device in which a complexly shaped separation channel representing one embodiment of the present invention is included.

The complexly shaped separation channel illustrated in FIGS. 2A-B may be employed within a subunit of a microfluidic device. FIG. 4 illustrates a representative subunit of a microfluidic device in which a complexly shaped separation channel representing one embodiment of the present invention may be included. In FIG. 4, a serpentine separation channel 402 connects an anode reservoir 404 with a cathode reservoir 406. A sample solution is injected into an injection port 408. The sample is electrokinetically driven towards a waste reservoir 410 to form a sample plug at the intersection with the separation channel 412. The plug can then be driven towards the cathode reservoir 406 by application of an electrical potential between the anode 404 and cathode 406 reservoirs. The microfluidics subunit 400 shown in FIG. 4 may be incorporated within a larger microfluidics chip used for identification and/or purification of biopolymers. For example, the separation channel 402 may be interconnected with a microinput line leading to various different crystallization chambers within an automated crystallization chip. As another example, microsensors may be oriented along the separation channel 402 in order to detect the bands of molecular species that migrate past the sensors under the influence of the applied electrical potential.

Microfluidics-chip implementations provide many advantages over macroscale devices. For example, such systems are useful in clinical laboratory settings where simple analytical protocols enabled by automation can significantly reduce errors. Microfluidics chips provide good heat dissipation, due to their large surface-to-volume ratios and additionally provide a relatively large thermal mass in contact with the separation channel. Microfluidics devices can be easily and economically mass produced, resulting in significant economy in biopolymer purification. Moreover, the relatively small chambers and channels allow for analytical and preparative processes to be carried out with small volumes and with little waste.

Figure 5:
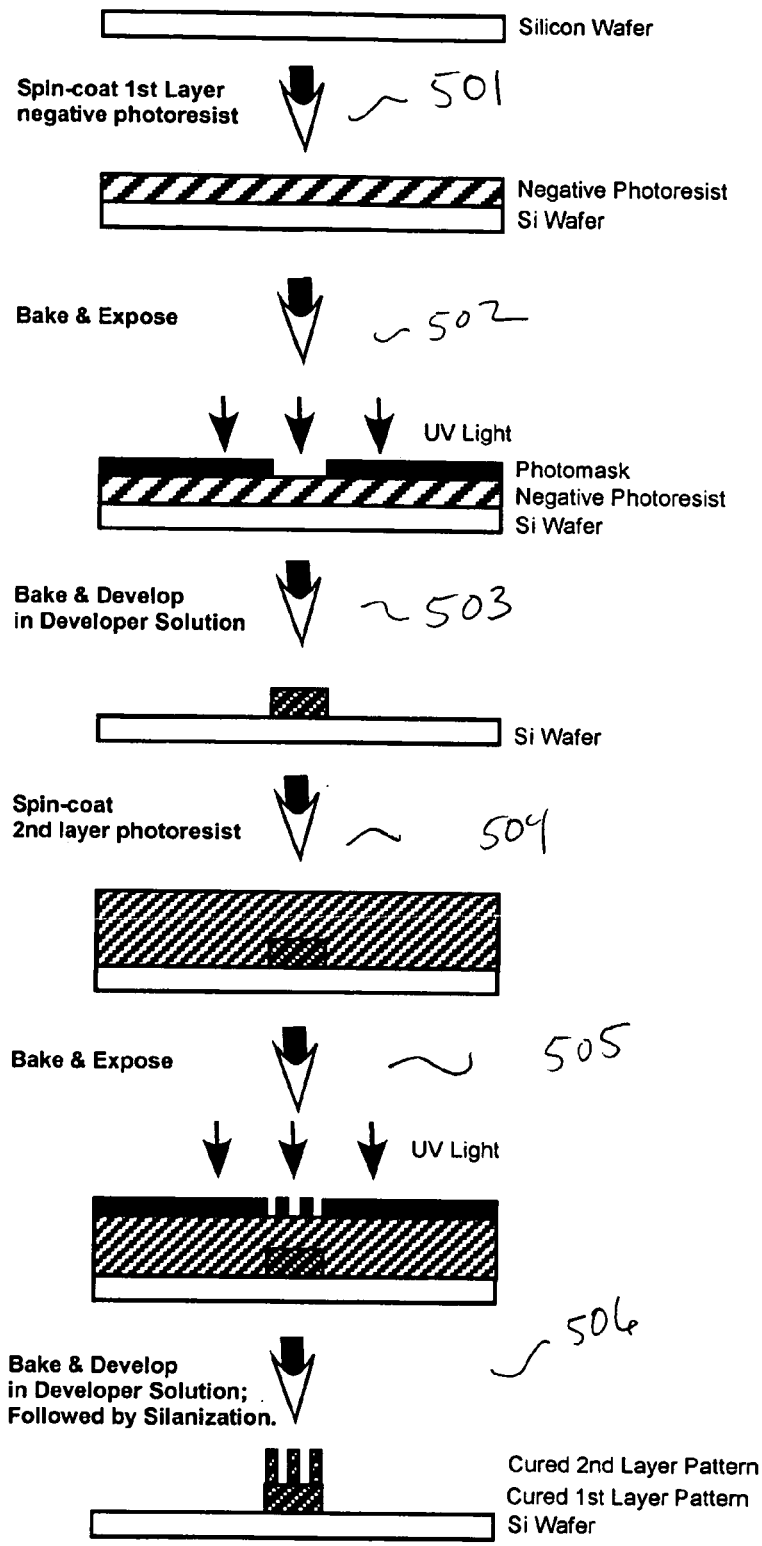
FIG. 5 illustrates the production of a molding master on a silicon wafer from which slabs incorporating microfluidics components can be replicated.

FIG. 5 illustrates the production of a molding master on a silicon wafer from which PDMS slabs incorporating microfluidics components can be replicated. First, in step 501, a negative photoresist is spun onto a silicon wafer. In step 502, the photoresist is baked, and then partially exposed to ultraviolet light through a patterned photomask using a mask aligner. The portion of the photoresist layer exposed to ultraviolet light is cross-linked by the UV radiation, and bees insoluble in developer solution. The portion of the photoresist not exposed to UV radiation remains soluble in developer solution. Exposing the photo resist layer to developing solution, in step 503, removes uncross-linked photoresist and leaves raised structures consisting of cross-linked photoresist on the surface of the silicon, essentially a negative, relief image of the original photomask. The application of photoresist and UV exposing steps can be repeated, shown in FIG. 5 as steps 505 and 506, to pattern a second photoresist layer above the first structures remaining on the silicon wafer to create multi-level, layered structures. The application of photoresist, UV exposure, and developing steps can be additionally repeated to add additional layers. After creation of the final, a final developing step 506 is carried out, and the resulting master mold is passivated with fluorosilane to allow a PDMS slab to be cast on the master mold and easily removed. In alternative methods, positive photoresist layers may be used to create positive, relief images. In yet other methods, microstructures can be produced by etching and by directed radiation beams.

Figure 6:
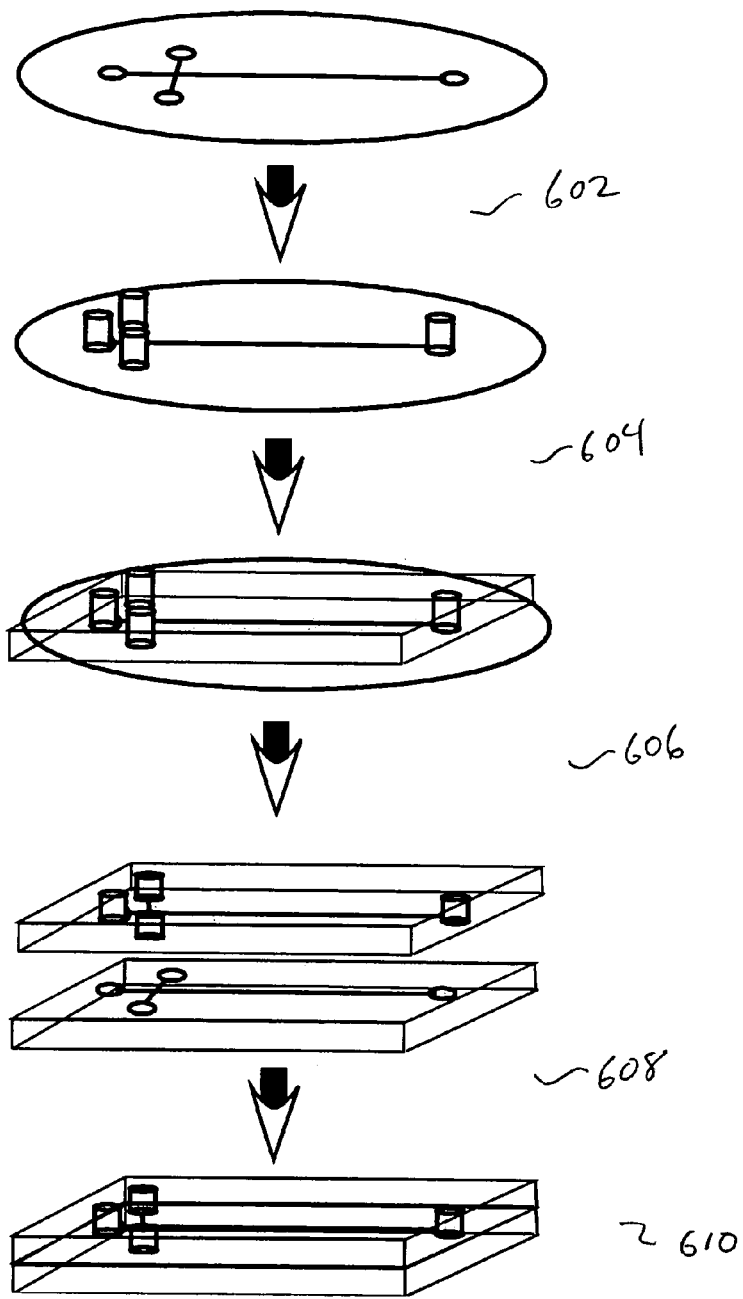
FIG. 6 illustrates production of a microfluidics device using a master mold.

FIG. 6 illustrates production of a PDMS microfluidics device using a master mold. First, the master mold is produced by photolithography and by additional surface modification in step 602. Next, in step 604 liquid PDMS is poured onto the surface of the master mold and baked in order to cure the liquid PDMS into a soft, semi-solid slab. Next, in step 606, the PDMS slab is removed from the master mold and oxidized in an oxygen plasma. Finally, in step 608, two complementary slabs, such as slabs 202 and 210 in FIG. 2A, are aligned and bonded together to produce the final microfluidics device or microfluidics-device subunit 610. If the components within a slab are bilaterally symmetrically arranged, two identical slabs produced from a single mold can be joined together to produce a final microfluidics device or microfluidics-device subunit. Otherwise, complementary slabs are created on two different, complementary master molds and joined to produce a final microfluidics device or microfluidics-device subunit.

Figure 7:
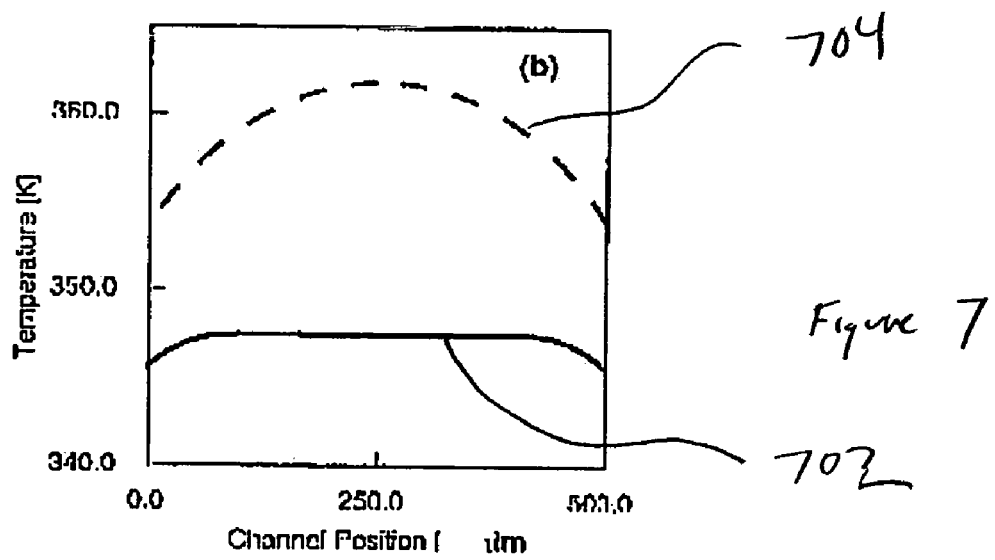
FIG. 7 shows a plot of the temperatures within a four-fin, complexly shaped separation channel computed across the cross-section of the complexly shaped separation channel in comparison with a plot of the temperatures computed across a cross-section of a simply shaped, rectangular separation channel.

FIG. 7 shows a plot of the temperatures within a four-fin, complexly shaped microscale separation channel computed across the cross-section of the complexly shaped separation channel in comparison with a plot of the temperatures computed across a cross-section of a simply shaped, rectangular separation channel. The plot of temperature versus position 702 for the complexly shaped microscale separation channel shows greater uniformity of temperature across the channel cross section than the plot of temperature versus position 704 for the simply shaped, rectangular separation channel. Uniformity of temperature across the cross section of a separation channel prevents thermal currents and corresponding bulk solution flow from developing. Also, the average temperature within the complexly shaped microscale separation channel is significantly lower than for the simply shaped, rectangular separation channel. Lowering of the average temperature prevents denaturing of biopolymers and heat-induced chemical reactions.

Figure 8:
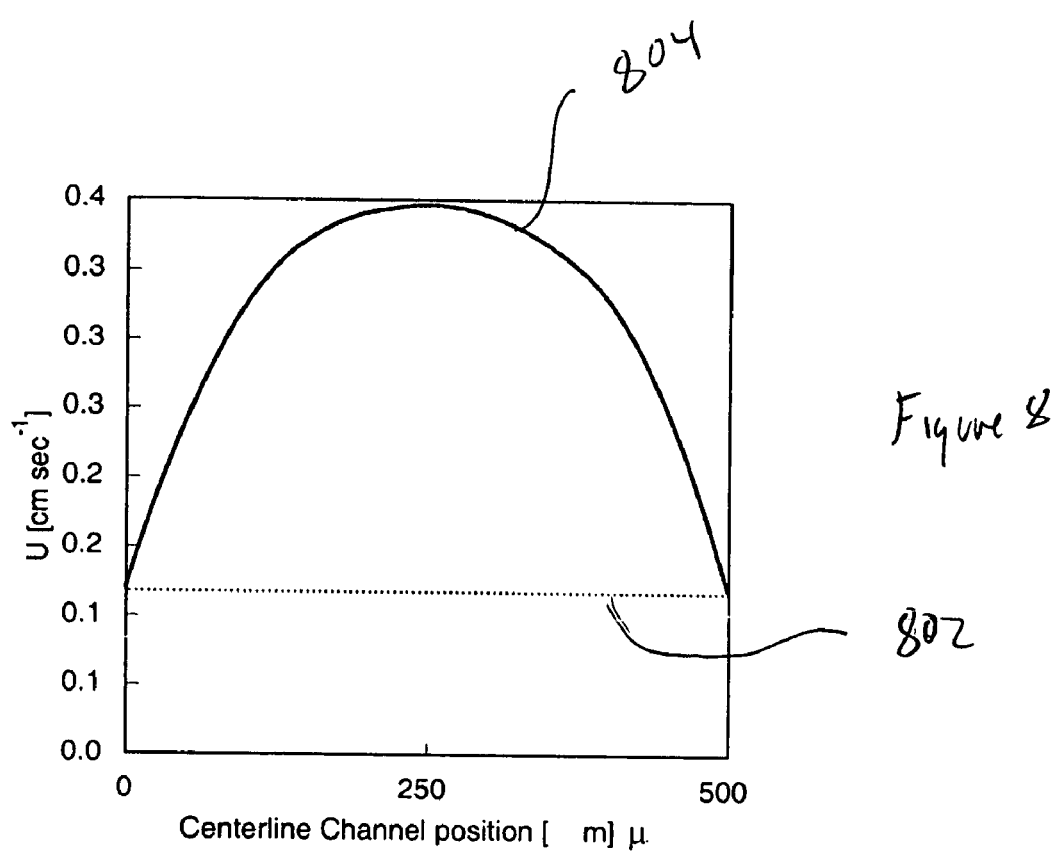
FIG. 8 shows plots of computed fluid velocities at different points across the cross-section of a simply shaped and complexly shaped separation channel.

FIG. 8 shows plots of computed fluid velocities at different points across the cross-section of a simply shaped and a complexly shaped separation channel. The plot for the complexly shaped channel 802 shows a constant fluid velocity across the complexly shaped channel, while the plot for the simply shaped channel 804 exhibits a familiar parabolic shape resulting from fluid-flow-velocity dependency on the distance from the center of the channel.

Although the present invention has been described in terms of a particular embodiment, it is not intended that the invention be limited to this embodiment. Modifications within the spirit of the invention will be apparent to those skilled in the art. For example, many different types of materials may be used to fabricate microfluidic separation channels with complex, non-convex cross-sections. Although complexly shaped separation channels with non-convex cross-sections may be uniquely suitable for microfluidics applications, complexly shaped separation channels may also be employed in traditional, large-scale separation-channel-based purification equipment, including HPLC, various types of column chromatography, and electrophoresis. The non-convex cross-sectional areas, as discussed above, allow for arbitrary surface-to-volume ratios greater than a minimum surface-to-volume ratio to be obtained regardless of the total internal volume of the separation channel. Thus, decreased resistance to hydrodynamic flow within a large, simply shaped separation channel and undesirable heat buildup within large, simply shaped separation channel can be ameliorated by using a complexly shaped separation channel with a non-convex cross section, regardless of the particular separation technique employed. The microscale manufacturing techniques described above may be employed to not only produce separation channels with non-convex cross sections, but also separation channels with other types of shape variations that may facilitate particular types of separations induced by various different separation techniques. As discussed above, materials from which complexly shaped separation channels can be made include glass, fused quartz, silicon, ceramics, and polymeric materials including polymethylmethacrylate, polydimethylsiloxane, polyethylene, polyester, polyvinyl chloride, fluoroethylpropylene, lexan, polyamide, polyimide, polystyrene, polycarbonate, cyclic olefin copolymers, polyurethane, polyestercarbonate, polypropylene, polybutylene, polyacrylate, polycaprolactone, polyketone, polyphthalamide, polysulfone, epoxy polymers, thermoplastics, fluoropolymer, and polyvinylidene fluoride, or another rigid, transparent material The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A separation channel incorporated within a molecular separation apparatus comprising:
    a hollow channel with a non-convex cross section; and
    interconnections at each end of the separation channel to additional fluid-managing components of the molecular separation apparatus; wherein two points may be selected on the boundary of the non-convex cross section so that, when a straight line is drawn between the two points, the straight line contains three line segments exterior to the non-convex cross section.

2. The separation channel of claim 1 wherein the separation channel is made from one of:
    glass;
    fused quartz;
    silicon;
    ceramics; and
    a polymeric material.

3. The separation channel of claim 2 wherein the polymeric material is one of, or a combination of two of: polymethylmethacrylate, polydimethylsiloxane, polyethylene, polyester, polyvinyl chloride, fluoroethylpropylene, lexan, polyamide, polyimide, polystyrene, polycarbonate, cyclic olefin copolymers, polyurethane, polyestercarbonate, polypropylene, polybutylene, polyacrylate, polycaprolactone, polyketone, polyphthalamide, polysulfone, epoxy polymers, thermoplastics, fluoropolymer, and polyvinylidene fluoride.

4. The separation channel of claim 1 wherein the separation channel is microfabricated, as part of a microfluidics device, from one or more polymeric materials.

5. The separation channel of claim 1 wherein the interconnections at each end of the separation channel couple the separation channel to one or more of:
    input and output channels;
    fluid reservoirs;
    analytical devices;
    force-applying components; and
    injection ports.

6. A separation channel incorporated within a molecular separation apparatus comprising:
    a hollow channel with a non-convex cross section; and
    interconnections at each end of the separation channel to additional fluid-managing components of the molecular separation apparatus; wherein two points may be selected on the boundary of the non-convex cross section so that, when a straight line is drawn between the two points, the straight line contains four line segments exterior to the non-convex cross section.

7. The separation channel of claim 6 wherein the separation channel is made from one of:
    glass;
    fused quartz;
    silicon;
    ceramics; and
    a polymeric material.

8. The separation channel of claim 7 wherein the polymeric material is one of, or a combination of two of: polymethylmethacrylate, polydimethylsiloxane, polyethylene, polyester, polyvinyl chloride, fluoroethylpropylene, lexan, polyamide, polyimide, polystyrene, polycarbonate, cyclic olefin copolymers, polyurethane, polyestercarbonate, polypropylene, polybutylene, polyacrylate, polycaprolactone, polyketone, polyphthalamide, polysulfone, epoxy polymers, thermoplastics, fluoropolymer, and polyvinylidene fluoride.

9. The separation channel of claim 6 wherein the separation channel is microfabricated, as part of a microfluidics device, from one or more polymeric materials.

10. The separation channel of claim 6 wherein the interconnections at each end of the separation channel couple the separation channel to one or more of:
    input and output channels;
    fluid reservoirs;
    analytical devices;
    force-applying components; and
    injection ports.

11. A separation channel incorporated within a molecular separation apparatus comprising:
    a hollow channel with a non-convex cross section; and
    interconnections at each end of the separation channel to additional fluid-managing components of the molecular separation apparatus; wherein two points may be selected on the boundary of the non-convex cross section so that, when a straight line is drawn between the two points, the straight line contains more than four line segments exterior to the non-convex cross section.

12. The separation channel of claim 11 wherein the separation channel is made from one of:
    glass;
    fused quartz;
    silicon;
    ceramics; and
    a polymeric material.

13. The separation channel of claim 12 wherein the polymeric material is one of, or a combination of two of: polymethylmethacrylate, polydimethylsiloxane, polyethylene, polyester, polyvinyl chloride, fluoroethylpropylene, lexan, polyamide, polyimide, polystyrene, polycarbonate, cyclic olefin copolymers, polyurethane, polyestercarbonate, polypropylene, polybutylene, polyacrylate, polycaprolactone, polyketone, polyphthalamide, polysulfone, epoxy polymers, thermoplastics, fluoropolymer, and polyvinylidene fluoride.

14. The separation channel of claim 11 wherein the separation channel is microfabricated, as part of a microfluidics device, from one or more polymeric materials.

15. The separation channel of claim 11 wherein the interconnections at each end of the separation channel couple the separation channel to one or more of:
  input and output channels;
  fluid reservoirs;
  analytical devices;
  force-applying components; and
  injection ports.

* * * * *

UNITED STATES PATENT AND TRADEMARK OFFICE
CERTIFICATE OF CORRECTION

| | | |
|---|---|---|
| PATENT NO. | : 7,524,409 B2 | Page 1 of 1 |
| APPLICATION NO. | : 10/846147 | |
| DATED | : April 28, 2009 | |
| INVENTOR(S) | : Daniel T. Chiu et al. | |

It is certified that error appears in the above-identified patent and that said Letters Patent is hereby corrected as shown below:

In the Specification

In Column 1, Line 12, after the section labeled CROSS-REFERENCE TO RELATED APPLICATION, please add the following section:

-- STATEMENT OF GOVERNMENT LICENSE RIGHTS

This invention was made with government support under RO1 GM065293 awarded by the National Institutes of Health. The government has certain rights in the invention. --

Signed and Sealed this
Fourth Day of November, 2014

Michelle K. Lee
*Deputy Director of the United States Patent and Trademark Office*